US009180447B2

(12) United States Patent
Schlegel et al.

(10) Patent No.: US 9,180,447 B2
(45) Date of Patent: Nov. 10, 2015

(54) PIPETTING DEVICE HAVING A LINEAR MOTOR

(75) Inventors: Andreas Schlegel, Maienfeld (CH); Hanspeter Romer, Gyrenbad (CH)

(73) Assignee: HAMILTON BONADUZ AG, Bonaduz (CH)

( * ) Notice: Subject to any disclaimer, the term of this patent is extended or adjusted under 35 U.S.C. 154(b) by 319 days.

(21) Appl. No.: 13/824,597

(22) PCT Filed: Dec. 23, 2011

(86) PCT No.: PCT/EP2011/073961
§ 371 (c)(1),
(2), (4) Date: Mar. 18, 2013

(87) PCT Pub. No.: WO2012/085274
PCT Pub. Date: Jun. 28, 2012

(65) Prior Publication Data
US 2013/0233096 A1    Sep. 12, 2013

(30) Foreign Application Priority Data

Dec. 23, 2010    (DE) .................. 10 2010 064 049

(51) Int. Cl.
| | |
|---|---|
| *B01L 3/02* | (2006.01) |
| *B66F 11/00* | (2006.01) |
| *B01L 9/00* | (2006.01) |

(Continued)

(52) U.S. Cl.
CPC .............. *B01L 3/0213* (2013.01); *B01L 9/54* (2013.01); *G01N 35/1067* (2013.01); *G01N 35/1072* (2013.01); *B01L 2200/021* (2013.01); *B01L 2200/025* (2013.01); *G01N 2035/1069* (2013.01)

(58) Field of Classification Search
CPC .......... G01N 35/1074; G01N 35/1079; G01N 35/10; G01N 35/1083; G01N 35/109; G01N 35/0604; G01N 35/1072; G01N 35/1011; G01N 35/1085; G01N 2035/1069; H02K 41/02–41/03; H02K 41/031; H02K 41/033
See application file for complete search history.

(56) References Cited

U.S. PATENT DOCUMENTS

| | | | |
|---|---|---|---|
| 2002/0083998 A1 | 7/2002 | Overbeck et al. | |
| 2003/0113232 A1* | 6/2003 | Reinhardt et al. | 422/99 |

(Continued)

FOREIGN PATENT DOCUMENTS

| | | |
|---|---|---|
| CN | 101405929 A | 4/2009 |
| DE | 197 00 392 A1 | 7/1997 |

(Continued)

OTHER PUBLICATIONS

"Linearmotor," Wikipedia [online] dated Aug. 16, 2011.

*Primary Examiner* — Eric S McCall
*Assistant Examiner* — Anthony W Megna Fuentes
(74) *Attorney, Agent, or Firm* — Rothwell, Figg, Ernst & Manbeck, P.C.

(57) ABSTRACT

The invention relates to a pipetting device, comprising at least two pipetting channels (50, 50'), which extend along a channel axis (K) and which each can be adjusted along the channel axis (K), wherein the pipetting device (10) has a displacement drive, by means of which each pipetting channel (50, 50') can be displaced independently of the other pipetting channel (50, 50') along a displacement axis (V) orthogonal to the channel axis (K) regardless of an adjustment along the channel axis (K), wherein the displacement drive comprises a linear motor, the stator of which has at least two magnet arrangements (32, 42), which comprise a row of magnets (36) on a magnet carrier (34, 44), said magnets being consecutive along the displacement axis (V) and being arranged differently with regard to the polarity (P1, P2) thereof, and the armature of which (at 38, at 38'); has at least one conductor loop arrangement (38), which comprises at least one set of three conductor loops (72, 74, 76) that are consecutive along the displacement axis (V), each of which conductor loops is or can be associated with a different phase of a three-phase supply, wherein each pipetting channel (50, 50') has at least one conductor loop arrangement (38, 38'), wherein the armatures (at 38, at 38') of two pipetting channels (50, 50') directly adjacent along the displacement axis (V) are associated with different magnet arrangements (32, 42) and interact therewith.

14 Claims, 7 Drawing Sheets

(51) Int. Cl.
*G01N 35/10* (2006.01)

(56) References Cited

U.S. PATENT DOCUMENTS

2007/0252444 A1* 11/2007 Sadakane et al. ............... 310/12
2008/0240898 A1* 10/2008 Manz et al. ................... 414/680

FOREIGN PATENT DOCUMENTS

| JP | 9 268 451 A | | 10/1997 | |
|----|----|----|----|----|
| JP | 2001245464 A | * | 9/2001 | ............. H02K 41/03 |
| JP | 2008160955 A | * | 7/2008 | |
| WO | 2005031316 A1 | | 4/2005 | |

* cited by examiner

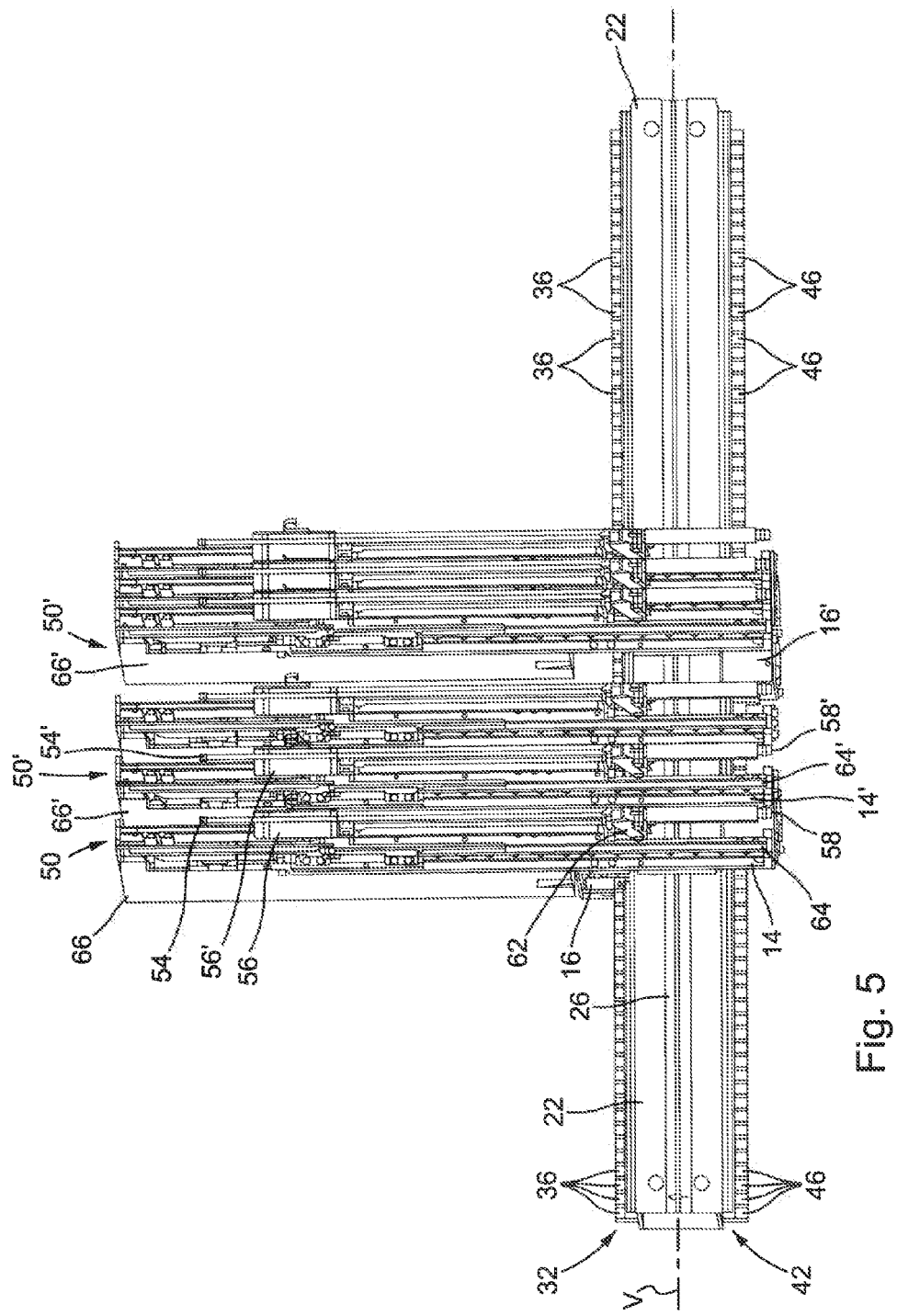

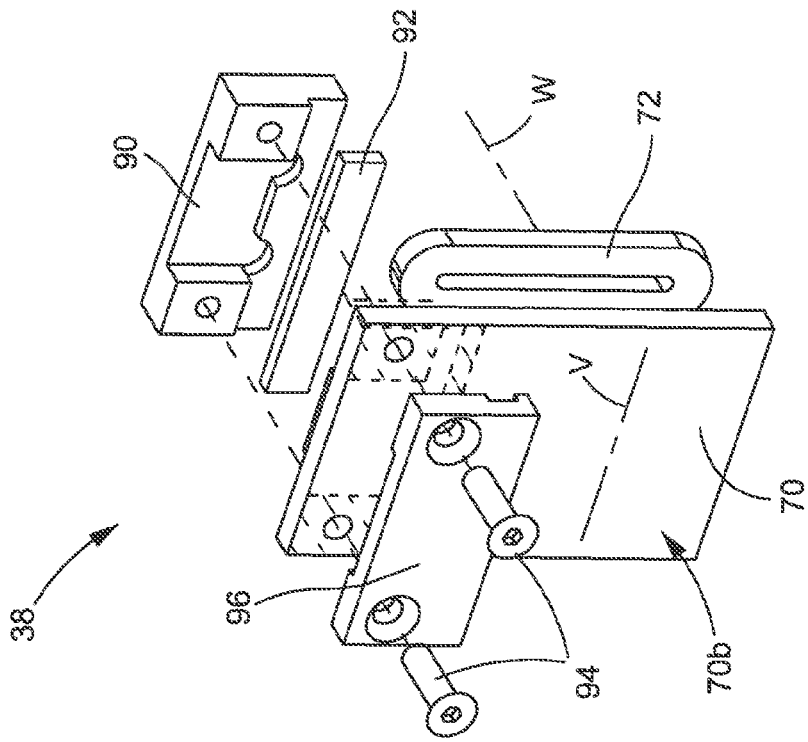
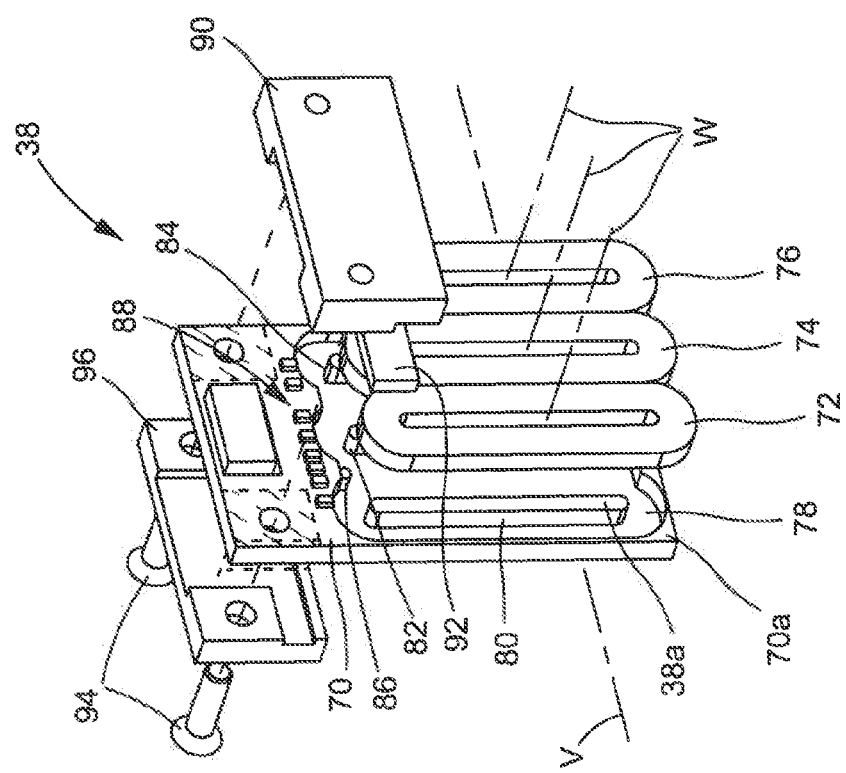

ered length dimension, which is determined by the winding turns of the conductor loop, does have to be conveyed completely past the magnet arrangement, but this does not mean that, at a given flow of current through the conductor loop arrangement, the force with which the conductor loop arrangement is displaced relative to the magnet arrangement is also a function of the displacement position of the conductor loop arrangement relative to the magnet arrangement.

PIPETTING DEVICE HAVING A LINEAR MOTOR

CROSS REFERENCE TO RELATED APPLICATION

This application is a 35 U.S.C. 371 National Phase Entry Application from PCT/EP2011/073961, filed Dec. 23, 2011, which claims the benefit of German Patent Application No. 10 2010 064 049.2 filed on Dec. 23, 2010, the disclosure of which is incorporated herein in its entirety by reference.

BACKGROUND OF THE INVENTION

1. Field of the Invention

The present invention relates to a pipetting device having at least two pipette channels which extend along a channel axis and whereof each may be adjusted along the channel axis, wherein the pipetting device has a displacement drive having a linear motor by means of which a pipette channel may be displaced along a displacement axis which is at a right angle to the channel axis, independently of adjustment along the channel axis.

2. Background of the Related Art

Pipetting devices of this kind are known from DE 10 2005 049 920 A1.

The stator of the known pipetting device has only one magnet arrangement with which a plurality of armatures interact, and each of these is itself coupled to a plurality of pipette channels. The pipette channels within a group associated with a common armature are only movable together along the displacement axis and are movable relative to one another in a direction of movement at a right angle to the displacement axis and at a right angle to the parallel channel axes, by means of spindle drives.

It is a disadvantage of the known pipetting device that the pipette channels all are associated with the same magnet arrangement and so restrict one another in their mobility, in particular in how close they may be brought to one another.

SUMMARY OF THE INVENTION

It is the object of the present invention to improve the displacement drive by using a linear drive of the pipetting device mentioned at the outset.

This is achieved according to the present invention by a pipetting device having all the features of Claim 1.

Conventionally, a linear motor includes a stator and an armature, it then being possible to provide the stator, which is conventionally of greater mass, stationary on a frame of the pipetting device, whereas the armature of the linear motor is coupled, for the purpose of moving together, to the pipette channel.

In principle, it is immaterial here whether the conductor loop arrangement forms the armature or the stator and whether the magnet arrangement forms the stator or the armature.

Because the stator extends over the entire displacement path along the displacement axis, according to the invention it is provided for the stator to have the magnet arrangement, which tends to have a greater mass per unit length, and for the armature to have the conductor loop arrangement. The conductor loop arrangement may be of short and hence low-cost construction.

Further, in the arrangement proposed it is possible, in an extremely advantageous manner, to move a plurality of pipette channels, each having separate conductor loop arrangements, on one and the same magnet arrangement. In cases where the stator is equipped with the conductor loop arrangement, this would only be possible with great complexity, since current flows through all the conductor loops at all times and thus all the pipette channels associated with a common stator would respond by means of their armatures to the flow of current through the conductor loop arrangement.

In principle, it is conceivable to equip the magnet arrangement wholly or in part with electromagnets. However, this is very complex and expensive. For cost reasons, it is therefore preferred for the magnet arrangement to include permanent magnets, and preferably to include only permanent magnets.

For the functioning of a linear motor, it is necessary for the conductor loop arrangement to be located in the magnetic field of the magnet arrangement. Here, however, in order to achieve a desirable reduction in the number of components required to construct the linear drive, it may be sufficient for a magnet arrangement to be provided only on one side of a conductor loop arrangement. This means that one side of the conductor loop arrangement is opposite a magnet arrangement while the opposite side of the conductor loop arrangement is not opposite a magnet arrangement.

In this case, it is preferable for the magnet arrangement, in particular if it includes permanent magnets, to be provided on a ferromagnetic support. Preferably, the magnets of the magnet arrangement are located between the ferromagnetic support and the conductor loop arrangement. A ferromagnetic support of this kind ensures an advantageous magnetic return path on the side of the magnet arrangement remote from the conductor loop arrangement and serves to intensify the action of the magnetic field emerging from the magnet arrangement towards the conductor loop arrangement.

Similarly, it is possible for the stator to include two substantially mutually parallel magnet arrangements between which a gap is formed in which a conductor loop arrangement is received such that it is movable along the displacement axis, wherein preferably unlike poles of magnets are opposite one another across the gap. In that case, the magnetic field lines running between the parallel magnet arrangements extend through the gap which is formed between the magnet arrangements and in which the conductor loop arrangement is received. Thus, a very effective magnetic field is provided for generating an electromagnetic propulsion on the conductor loop arrangement. However, it should be noted that the embodiment last mentioned is more expensive than the previously mentioned embodiment having a magnetic arrangement on only one side of the conductor loop arrangement, because of the second magnet arrangement that has to be provided. In the case of the embodiment last mentioned, having two parallel magnet arrangements forming a gap between them, a magnet arrangement is provided on each of two opposing sides of the conductor loop arrangement which are at a right angle to the coil axis of the conductor loops.

The embodiments mentioned above, of a pipette channel driven along the displacement axis by linear motor, make it possible to move the pipette channel along the displacement axis without play, because of the excellent properties of the linear motor thus formed. In particular, these embodiments provide the possibility of reversing without play the direction of movement along the displacement axis, which not only brings about an improvement on the mechanical displacement drives of pipette channels which have been used hitherto, but furthermore opens up the possibility of shaking off liquid which after pipetting undesirably adheres to the outside of a pipette tip that is coupled to the pipette channel, by operating the displacement drive with a plurality of reversals to the direction of movement in quick succession. The pipette tip can thus be set in oscillating motion along the displacement axis by the displacement drive operated by linear motor, as a result of which liquid that undesirably wets the outside of the pipette tip can be discarded or shaken off.

Furthermore, the use of a magnet arrangement and a conductor loop arrangement makes it possible, when the conductor loop arrangement is associated, as an armature, with the pipette channel as in the present invention and the magnet arrangement is associated with a fixed frame of the pipetting arrangement, to form a pipetting device having at least two pipette channels which may be displaced along the displacement axis. Because according to the invention each of these pipette channels includes a conductor loop arrangement which is separate from the conductor loop arrangement of the respectively other pipette channel, the two pipette channels may be displaced along the displacement axis independently of one another, by a corresponding flow of current through their respective conductor loop arrangement. In that case, it is further advantageous if the device includes a control unit which allows three-phase current to be applied to at least two conductor loop arrangements associated with different pipette channels, independently of one another, in order to provide the independent displaceability of the at least two pipette channels that may be displaced along the displacement axis.

The number of pipette channels that may be arranged on a single pipetting device increases with the number of magnet arrangements provided on the pipetting device. For this reason, according to the present invention it is provided for more than one magnet arrangement to be provided on a pipetting device.

Further, it may be that the dimension of a conductor loop arrangement or another component of the pipette channel in the direction of the displacement axis is greater than the dimension of the pipette channel in the same direction. In that case, the dimensions of the conductor loop arrangement or the other components of individual pipette channels along the displacement axis determine how close two pipette channels which are directly adjacent along the displacement axis may be brought to one another along the displacement axis.

According to the invention, the minimum spacing which may be achieved between two pipette channels which are directly adjacent along the displacement axis may be halved if the device includes at least two magnet arrangements, with the armatures of two pipette channels which are directly adjacent along the displacement axis being associated with different magnet arrangements and interacting therewith.

An armature interacts with a magnet arrangement in the context of the present application if it is located in the magnetic field of the magnet arrangement for generating a propulsion along the displacement axis. In that case it is also associated with this magnet arrangement.

Similarly, the minimum spacing which may be achieved between two pipette channels which are directly adjacent along the displacement axis if only a single magnet arrangement is provided may be quartered if the device has four magnet arrangements and at least four pipette channels which may be displaced along the displacement axis and which each have an armature, with each armature of a group of four pipette channels which directly succeed one another along the displacement axis being associated with a different magnet arrangement and interacting therewith.

In general, the spacing in the direction of the displacement axis between two pipette channels which are directly adjacent along the displacement axis may be reduced if k magnet arrangements are provided, wherein, for each group of k pipette channels which directly succeed one another along the displacement axis, each armature of this group is associated with a different magnet arrangement and interacts therewith. In that case, the total number of pipette channels of the pipetting device may exceed the value k. Here, k is a natural number.

So that the construction of the pipetting device according to the invention may be as short as possible in the dimension both at a right angle to the channel axis and also at a right angle to the displacement axis, it is advantageous if the at least one magnet arrangement is provided such that the magnets, whereof the magnetic field interacting with the application of current to a conductor loop arrangement located in the magnetic field for providing decisively the propulsion of the conductor loop arrangement, are arranged such that their direction of polarisation is oriented at a right angle to a plane that is both parallel to the channel axis and parallel to the displacement axis.

In this application, the term "direction of polarisation of a magnet" means the direction in which the south pole of a magnet succeeds its north pole.

Advantageously, the pipette channel axes lie in a common plane extending in the direction of the displacement axis. As a result of this, the dimension of the pipetting device at a right angle to the channel axes and at a right angle to the displacement axis may be kept advantageously small. Preferably, the common plane of the channel axes is a plane of symmetry with the pipetting device, for the purpose of facilitating assembly.

To provide assistance also from the point of view of motion guidance technology to the improvement achieved by the linear motor configuration according to the invention in how close to one another directly adjacent pipette channels may be brought, it may be provided for the pipetting device to have at least two linear guidance rails, wherein the pipette channels whereof the armatures are associated with the same magnet arrangement are guided on the same linear guidance rail, in a manner displaceable along the displacement axis. Advantageously, a linear guidance rail, in particular specifically one linear guidance rail, is provided in the pipetting device for each magnet arrangement.

A compact pipetting device may be obtained if it has one or two support profiles extending along the displacement axis, with each support profile supporting two magnet arrangements and two linear guidance rails, wherein it is possible for the purpose of facilitating assembly to provide for each support profile to be constructed substantially symmetrically in relation to a plane of symmetry extending along the displacement axis. In addition or as an alternative, it may be provided for it to have specifically two parallel support profiles, which are constructed substantially symmetrically in relation to a plane of symmetry extending along the displacement axis and located between the support profiles, with the plane of symmetry located between the support profiles preferably with the plane containing the channel axes.

It is possible to form a conductor loop arrangement which is short in its dimensions, in particular those along the displacement axis, simply and at low cost if the conductor loop arrangement includes a conductor board in which there is provided a recess for at least one conductor loop, in which the conductor loop is at least partly accommodated. Advantageously, the conductor loop arrangement only includes specifically one set of specifically three conductor loops.

Preferably, the conductor loop is, for the purpose of it being better protected from undesirable displacement and parts thereof entirely accommodated in the recess in the conductor board.

So that all the conductor loops in a conductor loop arrangement have preferably substantially the same constructional layout, preferably a respective recess of this kind is provided for a plurality of conductor loops, particularly preferably for all the conductor loops.

The conductor loops include a coil wire whereof the thickness or diameter is smaller than the thickness or diameter of the conductor loop. Preferably, the conductor loop includes windings which starting from a coil axis are adjacent to one another in a radial direction and windings which are adjacent in the axial direction, that is to say in the direction of the depth of the recess. In this way, when current passes through a conductor loop of this kind a locally strong magnetic field is generated, which interacts well with the magnetic field of the magnet arrangement in which it is located.

So that the conductor loops of the conductor loop arrangement can be mechanically protected as well as possible from external factors, it is further advantageous if the recess in the conductor board is made, starting from a side face thereof, in the direction of the thickness of the conductor board to a depth smaller than the thickness of the conductor board. In this way, a conductor loop of the conductor loop arrangement is surrounded by material of the conductor board on at least three sides and hence mechanically protected.

A conductor loop arrangement which is as thin as possible in the direction of the preferably parallel coil axes of the conductor loops may in this case be obtained if the conductor loops of a set succeed one another along the displacement axis without overlap.

Preferably, the dimension of the recess in the direction of the thickness of the conductor board corresponds to the dimension of the conductor loop to be accommodated therein, with the result that once the conductor loop has been arranged in the recess it is substantially flush with the outer face of the conductor board in which the recess is made. However, this is not mandatory. Where the important issue is that the conductor loop arrangement is short in the direction of the displacement axis, it may be just as preferable for the conductor loops of a set to be provided such that two conductor loops which are directly adjacent along the displacement axis, and preferably all three conductor loops which succeed one another directly along the displacement axis, overlap one another along the displacement axis.

A particularly thin conductor loop arrangement may be desirable if for example the conductor loop arrangement is to be received in the above-mentioned gap between two parallel magnet arrangements, since in that case the gap may be made correspondingly small. However, the possibility that the conductor loops whereof a magnet arrangement is opposite only one side may also be constructed to be thin is in no way to be ruled out.

Furthermore, to improve the magnetic flux it is conceivable for the magnets of a magnet arrangement to be arranged in a so-called "Halbach" array, that is to say that between two operating magnets, which substantially provide the magnetic field required for the propulsion of the conductor loop arrangement associated with them, there is arranged in each case a flux magnet whereof the direction of polarisation is substantially at a right angle to each of the directions of polarisation of the directly adjacent operating magnets. Conventionally, the directions of polarisation of directly adjacent operating magnets are directed in opposing directions and extend in the direction of the coil axes of the conductor loops.

BRIEF DESCRIPTION OF THE DRAWINGS

The present invention will be described in more detail in the drawings which follow, with reference to an embodiment according to the invention. In the drawings:

FIG. 5 shows a perspective front view of the pipetting device of FIGS. 3 and 4, FIG. 6 shows a perspective exploded view of a conductor loop arrangement forming an armature of the present pipetting device, obliquely from in front, FIG. 7 shows a perspective exploded view of the conductor loop arrangement in FIG. 6, obliquely from behind.

DETAILED DESCRIPTION

Figure 1:
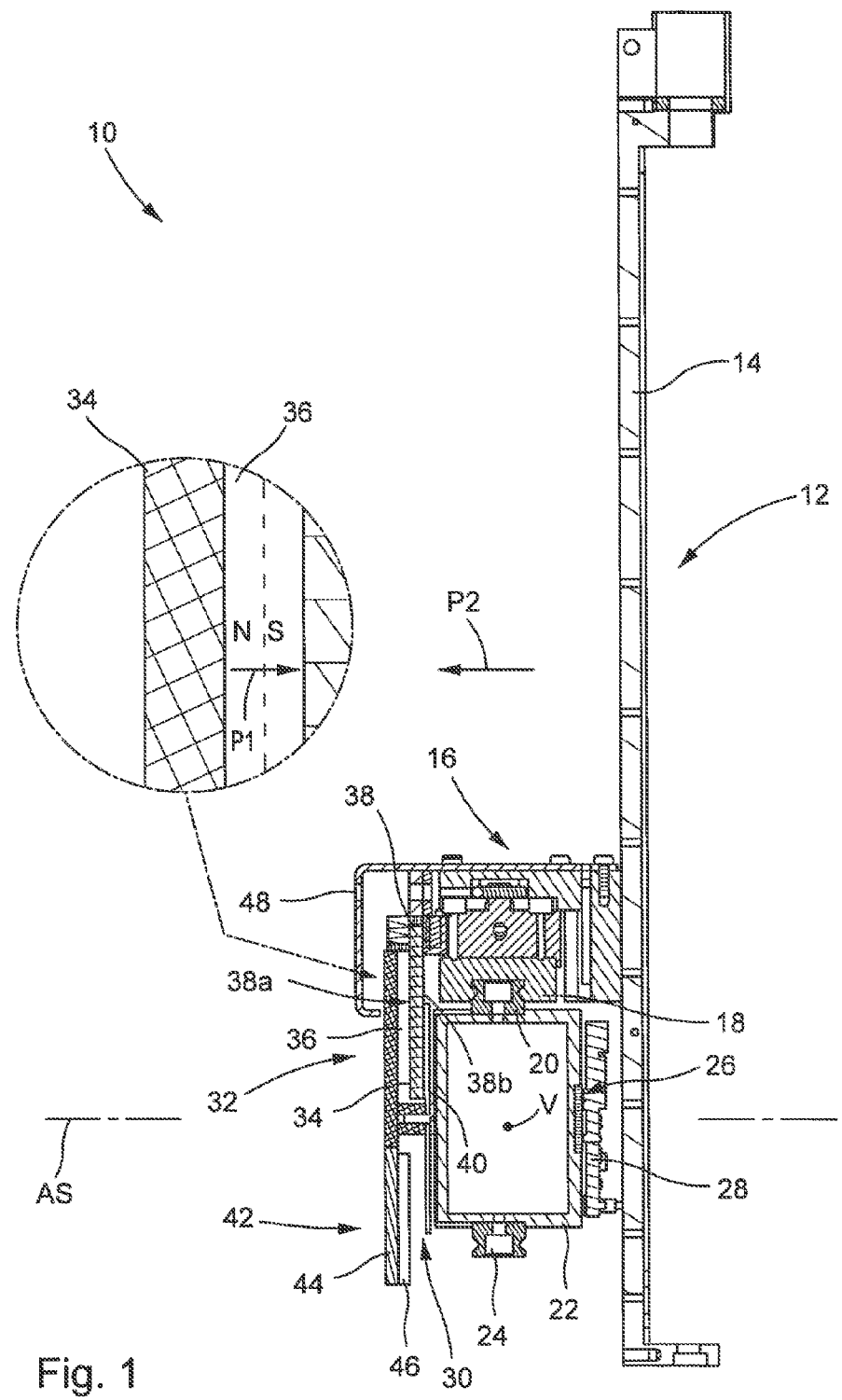
FIG. 1 shows a cross-sectional view of part of a pipetting device according to the invention, with the direction of view along the displacement axis and with the plane of section at a right angle to the displacement axis.

In FIG. 1, whereof the plane of the drawing is oriented at a right angle to the displacement axis V, a frame of a pipette channel of a pipetting device 10, this frame being drivable by linear motor along the displacement axis V, is generally designated 12.

The frame 12 includes a pipette channel support 14 on which, as illustrated below in FIG. 3, a pipette channel 50 may be arranged (see FIG. 3).

The pipette channel support 14 is connected, by way of a connection structure 16 which is of no further interest here, to a carriage 18 of a linear guidance device for the purpose of joint movement with the carriage 18. The linear guide carriage 18 is guided in a manner known per se on a linear guidance rail 20 such that it is displaceable along the displacement axis V. For this purpose, the linear guidance rail 20 extends along the displacement axis V and is fixed on a support profile 22 (in this case a square support profile) that also extends along the displacement axis V. The support profile 22 has a further guidance rail 24 which is fixed on the support profile 22, parallel to the guidance rail 20. In the example illustrated, the linear guidance rails 20 and 24 are located on opposing outer faces of the support profile 22.

The linear guidance rail 24 also serves—as will be described below in the context of FIG. 2—to guide the movement of pipette channel supports along the displacement axis V.

On the side of the support profile 22 facing the pipette channel support 14, a coding scale 26 is provided, with which there interacts a reader device 28, which is connected to the pipette channel support 14 for the purpose of common displacement, for determining the position of the pipette channel support 14 along the displacement axis V in a manner known per se.

Provided on the side of the support profile 22 remote from the pipette channel support 14, by way of a mounting 30, is a magnet arrangement 32 which has on a ferromagnetic support plate 34 permanent magnets 36 which are provided successively along the displacement axis V with alternating directions of polarisation. For example, the permanent magnets 36 may be glued to the ferromagnetic support plate 34.

In the present application, the term "direction of polarisation" of a permanent magnet means the direction in which the south pole of the magnet succeeds the north pole of the same magnet.

For example, the permanent magnet 36, visible in FIG. 1, of the upper magnet arrangement 32 may be oriented in respect of its polarisation such that its north pole lies on the ferromagnetic support plate 34, in other words pointing towards it, while the south pole of the same magnet points away from the ferromagnetic support plate 34 and towards the pipette channel support 14. In this case, the direction of polarisation of this permanent magnet 36, as illustrated in the drawing detail in FIG. 1 as direction of polarisation P1, is at a right angle to the displacement axis and at a right angle to the plane in which the ferromagnetic support plate 34 extends, pointing away therefrom.

The neighbouring permanent magnet following along the displacement axis, which succeeds the permanent magnet 36 that is visible in FIG. 1, therefore has a direction of polarisation P2 which is opposed to the direction of polarisation P1. The next-but-one permanent magnet is arranged with its direction of polarisation P1 in accordance with the permanent magnet 36 discussed above, and so on.

Arranged in the magnetic field of the magnet arrangement 32, in which the ferromagnetic support plate 34 ensures that there is an advantageous magnetic return path the permanent magnet 36 provided succeeding one another along the displacement axis V, is a conductor loop arrangement 38 which is provided on the connection structure 16 for the purpose of common movement therewith along the displacement axis V.

In the example illustrated, only the side 38a of the conductor loop arrangement 38 which points away from the pipette channel support 14 has a magnet arrangement 32 lying opposite it, while there is opposite the side 38b pointing towards the pipette channel support 14 no magnet arrangement but only a protective plate 40.

The mounting 30 is substantially symmetrical in respect of a plane of symmetry AS that extends in the direction of the displacement axis V and is at a right angle to the plane of the drawing in FIG. 1 and to the plane in which the ferromagnetic support plate 34 mainly extends, with the result that in FIG. 1 a further magnet arrangement 42 is provided below the magnet arrangement 32 and in turn has a ferromagnetic support plate 44 with permanent magnets 46 mounted thereon. The magnet arrangement 42 is of substantially the same construction as the magnet arrangement 32 described above, in other words having a row of permanent magnets which succeed one another along the displacement axis V with alternating directions of polarisation.

The connection structure 16 has a protective plate 48 which reaches over the magnet arrangement 32 in order to protect the air gap located between the magnet arrangement 32 and the conductor loop arrangement 38 from the ingress of dirt.

Figure 2:
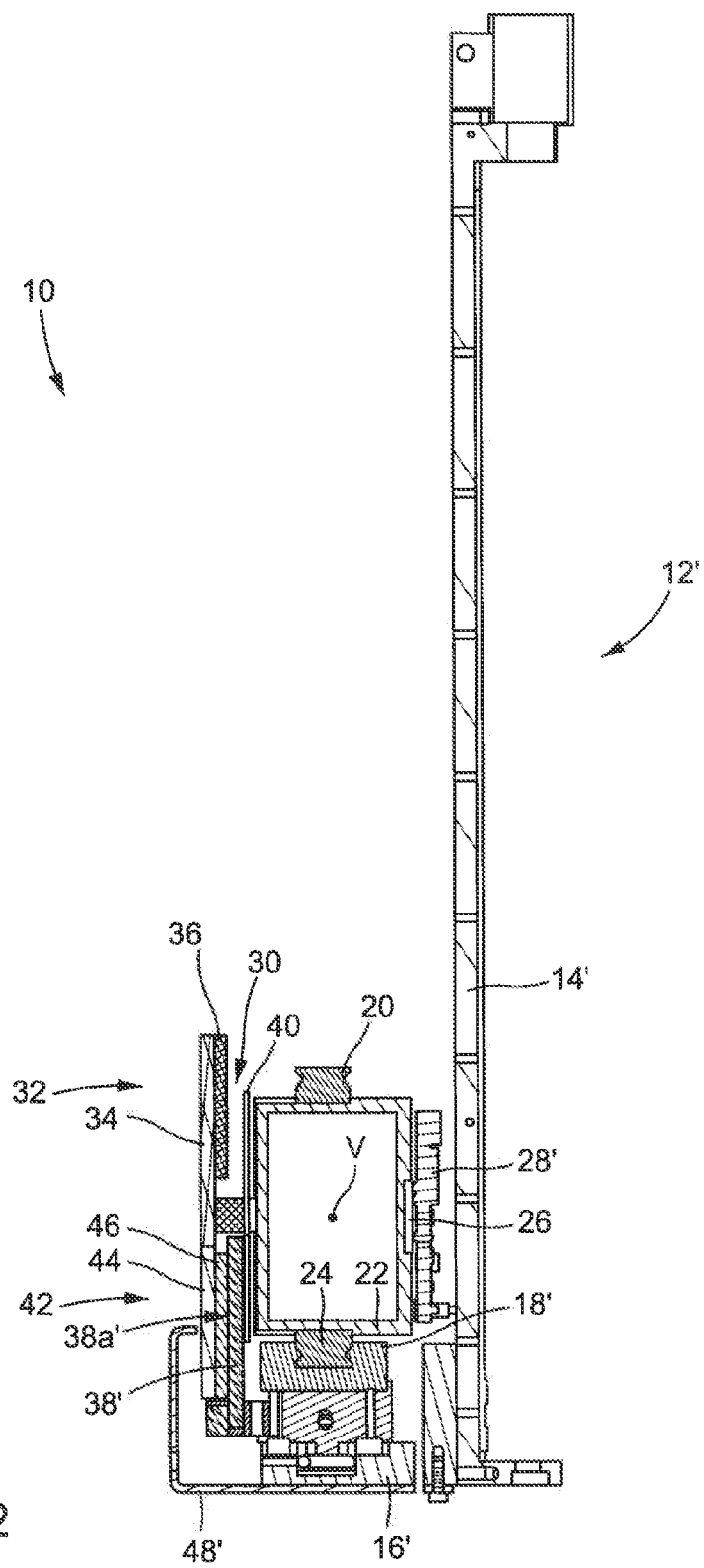
FIG. 2 shows another part of the same pipetting device, corresponding to that in FIG. 1 from a functional point of view.

In FIG. 2, the support profile 22 is shown in section through another axial point in relation to the displacement axis V, with a plane of section parallel to the plane of section in FIG. 1.

It shows a frame 12' which is directly adjacent, along the displacement axis V, to the frame 12 that may be displaced by linear motor in FIG. 1 and which may also be displaced by linear motor.

Components and component portions of the frame 12' that may be displaced by linear motor which are similar and have similar functions are provided with the same reference numerals as the corresponding components and component portions of the frame 12 that may be displaced by linear motor in FIG. 1 but are distinguished therefrom by an apostrophe.

The illustration in FIG. 2 is only described where it differs from that in FIG. 1, to the description whereof explicit reference is made.

The essential difference between the frames 12 and 12' that may be displaced by linear motor is that the frame 12' is guided such that it may be displaced along the displacement axis V by means of a guide carriage 18' on the linear guidance rail 24 on the support profile 22. For this reason, the conductor loop arrangement 38a', which is coupled to the connection structure 16' for common movement along the displacement axis V, is associated with the magnet arrangement 42 that is lower down in FIGS. 1 and 2, and interacts therewith.

Because of the alternating guidance of pipette channel supports 14 and 14' which directly succeed one another along the displacement axis V on the upper guidance rail 20 and the lower guidance rail 24, the pipette channel supports 14 and 14' and the pipette channels secured operatively thereto (see FIG. 3) may be brought closer to one another in the direction of the displacement axis V, since the guide carriages 18 and 18' and the connection structures 16 and 16' accommodated thereon and having the conductor loop arrangements 38 and 38' can overlap in the axial direction, which would not be possible if all the frames 12 and 12' were guided on a single linear guidance rail. The amount of axial overlap thus forms the gain in the amount by which they are brought axially closer to one another by using two parallel guidance rails 20 and 24.

Figure 3:
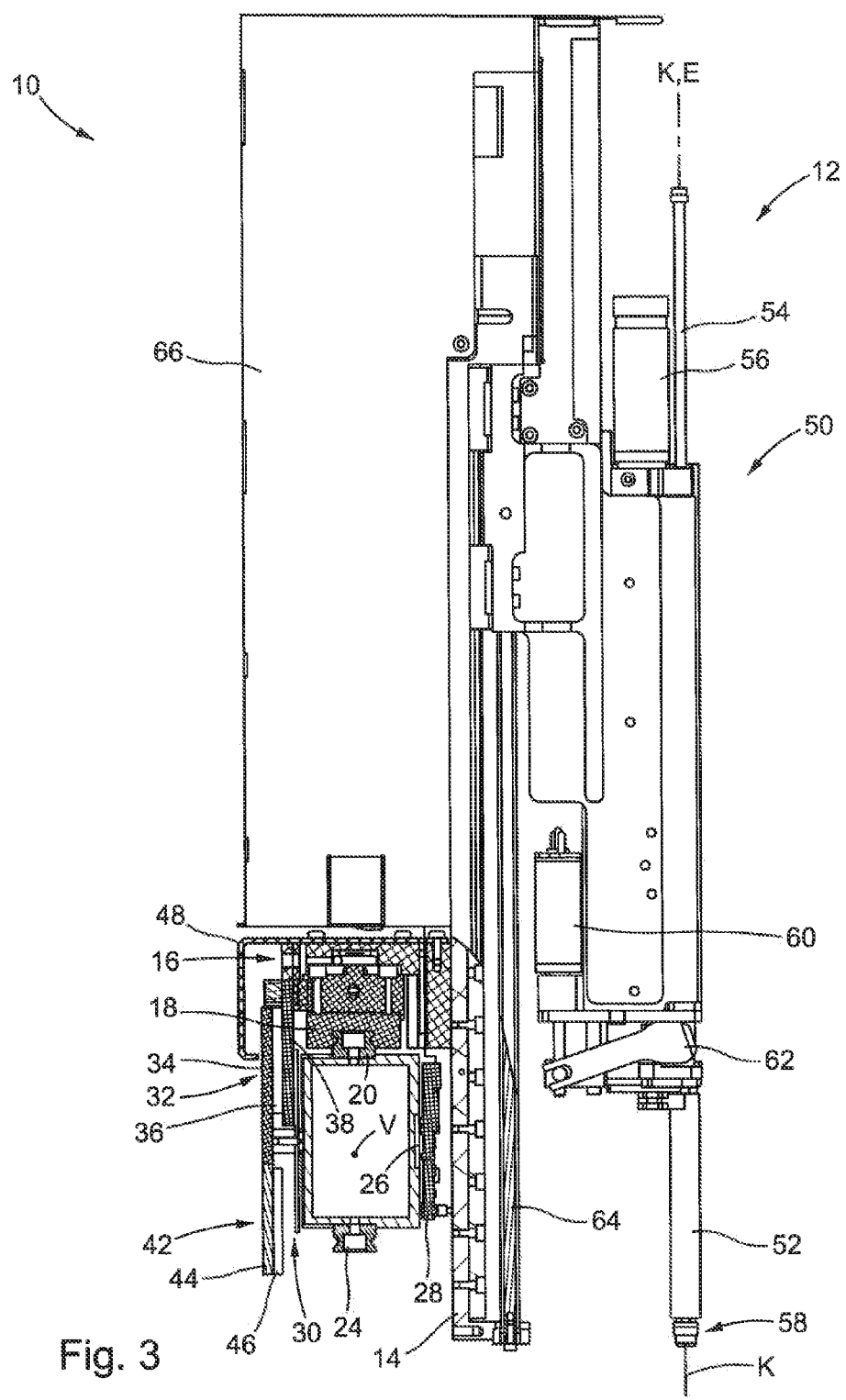
FIG. 3 shows the part of the pipetting device in FIG. 1, supplemented by its pipette channel and electronics.

FIG. 3 illustrates the frame 12 in FIG. 1, equipped with a pipette channel 50.

The pipette channel 50 is accommodated on the pipette channel support 14 and has the channel axis K, which extends at a right angle to the displacement axis V.

The pipette channel 50 has a cylinder 52 and a piston 54 which is movable in the cylinder 52 in relation thereto along the channel axis K and is drivable by the piston drive 56.

At its longitudinal end 58 closer to the dosing point, the cylinder 52 or the pipette channel 50 has a coupling geometry which is known per se, having a compression ring for coupling pipette tips. The coupling mechanism for holding pipette tips (which are not illustrated) on the pipette channel 50 and releasing them therefrom is actuated by a coupling drive 60, which is known per se and has a coupling gear 62.

Further, the frame 12 that may be moved by linear motor has a guidance rail 64 which extends in the direction of the channel axis K and on which the pipette channel 50 is provided such that it is movable along the channel axis K. Movement of the pipette channel 50 along the channel axis K on the guidance rail 64 is also preferably by motor.

To control the individual drives, in particular including driving of the frame 12 by linear motor, the pipette channel 50 is connected to electronics 66 in which control units and signal lines and power supply devices and lines are provided in order to trigger the individual drives in accordance with control commands. In particular, the electronics 66 are able to supply the conductor loop arrangement 38 with three-phase current, with the result that, interacting with the detection of position by the reader device 28 on the coding 26, the frame 12 may be displaced precisely into a desired position along the displacement axis V.

The electronics 66 may in turn be coupled to a central input/output device (not illustrated) and/or to a storage device. For example, the electronics 66 may receive control commands by way of a program or manual input, for example by way of a keyboard, touchscreen or the like.

It should further be pointed out that all the channel axes K of a pipetting device 10 preferably lie in a plane extending in the direction of the displacement axis V. In order to obtain a pipetting device of advantageously small depth, the planes in which the magnet arrangements 32 and 42 mainly extend are preferably parallel to the plane formed by the channel axis (or axes) K and the displacement axis V. The arrangement illustrated in FIG. 3 may additionally be present in mirror image with a plane of symmetry E including the channel axes K, in order to increase the density of pipette channels 50.

Figure 8:
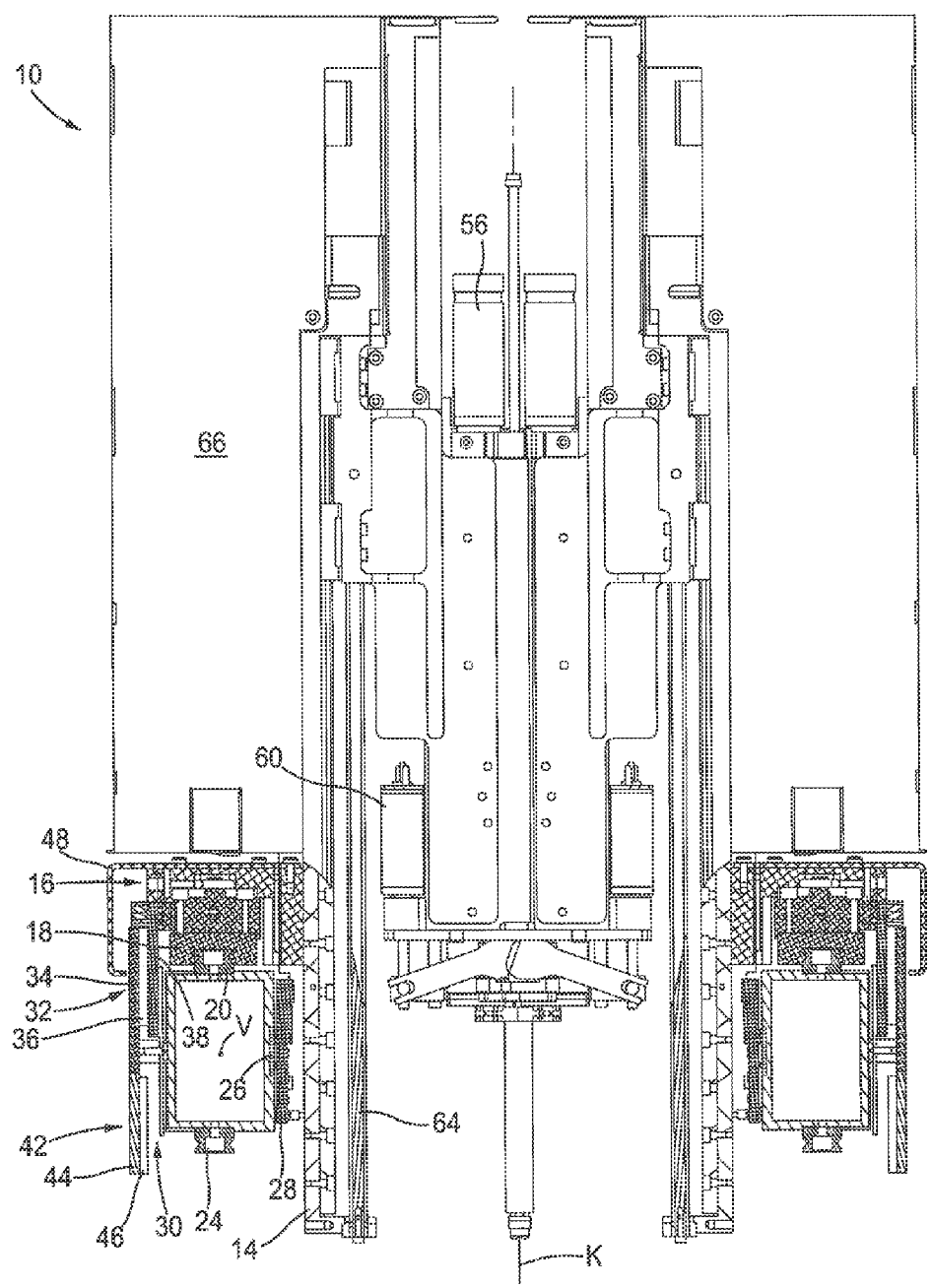
FIG. 8 shows the pipetting device in FIG. 3 with a second support profile.

In that case, there are therefore two parallel support profiles 22 each having two magnet arrangements 32 and 42 for each support profile, with the pipette channels lying between the two support profiles. This is illustrated schematically in FIG. 8. FIGS. 3 and 8 represent views of the present pipetting device from the same perspective.

In this case, it is advantageous if, for each group of four pipette channels which directly succeed one another along the displacement axis V, the conductor loop arrangement of each pipette channel from this group of four is associated with a different magnet arrangement and interacts therewith.

Because in that case the conductor loop arrangement, guide carriage, connection structure and pipette channels of a group of four of this kind can overlap one another axially, it is possible to bring directly successive pipette channels axially even closer to one another than is the case with only two guidance rails and one support profile.

Figure 4:
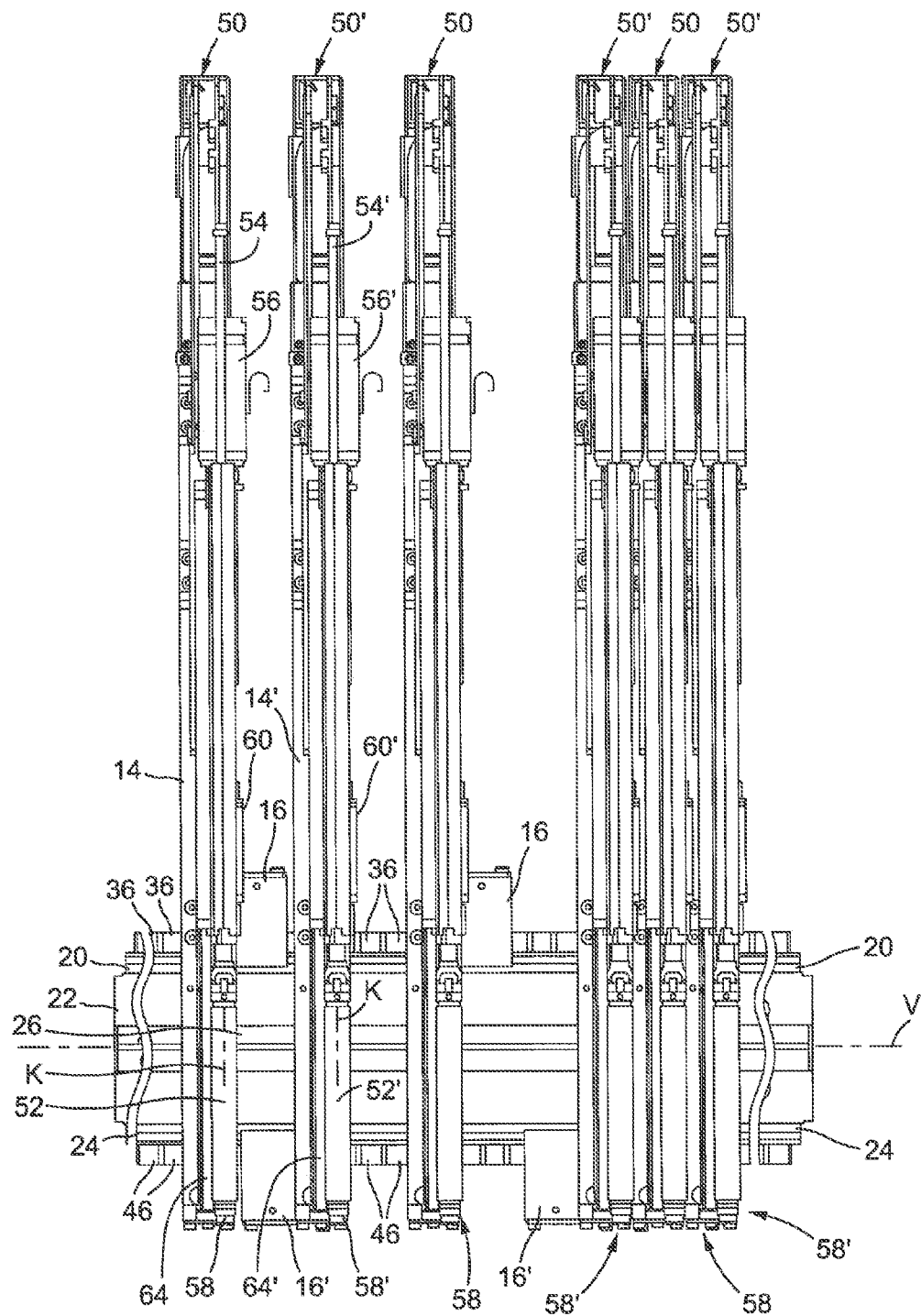
FIG. 4 shows the pipetting device in FIG. 3, in the front view according to the direction of view IV in FIG. 3.

FIG. 4 illustrates in front view the portion of the pipetting device 10 illustrated in FIG. 3. FIG. 5 shows the pipetting device 10 in FIG. 4, turned slightly to the side.

Visible in these drawings are the rows of permanent magnets 36 and 46 for forming the magnet arrangements 32 and 42.

FIG. 6 illustrates a conductor loop arrangement 38 in a perspective exploded view, obliquely from the front. It includes a conductor board 70 made of a synthetic material, such as a synthetic resin, on a side 70a whereof which is at a right angle to the coil axis W of the conductor loops 72, 74 and 76 there is provided a recess 78 in which the coils 72, 74 and 76 are laid. Each of the conductor loops 72, 74 and 76 is associated with a different phase of a three-phase current supply and is connectable or connected thereto.

Webs 80, 82 and 84 in the recess 78 simplify the arrangement and seating of the conductor loops 72, 74 and 76 in the recess 78, since the webs 80, 82 and 84 can be engaged in recesses located centrally within the coils 72, 74 and 76.

The coil wires of the individual conductor loops 72, 74 and 76 are wound around the coil axes W in the same direction of winding. Here, the coil wires are dimensioned such that windings of the conductor loops 72, 74 and 76 are adjacent both in the radial direction and in the axial direction in relation to the respective coil axis W.

When the conductor loop arrangement 38 is fully assembled, the side 70a of the conductor board 70 coincides with the side 38a of the conductor loop arrangement 38 which in FIGS. 1 to 3 points towards the respective associated magnet arrangement.

Starting from the side face 70a, in the direction of the coil axes W, that is to say in the direction of the depth of the conductor board 70, the recess 78 is dimensioned such that the conductor loops 72, 74 and 76 can be accommodated flush therein. To put it another way, the depth of the recess 78 corresponds substantially to the axial extent of the conductor loops 72, 74 and 76.

Air gaps remaining between the conductor board 70 and the conductor loops 72, 74 and 76 once the conductor loops 72, 74 and 76 have been laid in the recess 78 may be filled in using a flowable synthetic material, such as a synthetic resin, in order to improve the retention and seating of the conductor loops 72, 74 and 76 in the conductor board 70.

A temperature sensor 86 may be provided on the conductor board 70 in order to increase the operational safety of the conductor loop arrangement 38 and the linear motor drive as a whole.

Further, the conductor board 70 may have terminal contacts 88 which are prepared for electrical connection of the conductor loops 72, 74 and 76.

To secure the conductor loop arrangement 38, a securing basis 90 may be provided which makes contact with the conductor board 70 in the right-angled corner regions of the latter, which are shown with dot-and-dash hatching, and clamps a thermally conductive film 92 between the conductor board 70 and itself. The securing basis 90 is preferably made of aluminium in order to save weight (with a given component volume and a given component strength) and to provide good thermal conductivity properties. The thermally conductive film 92 may be made of silicone.

Provided on the rear side 70b of the conductor board 70 (see FIG. 7), by way of screws 94, is a clamping piece 96 which makes contact with the rear side 70b of the conductor board 70 along the regions which are shown in FIG. 7, also with dot-and-dash hatching. In this way, the conductor board 70 is held between the securing basis 90 and the clamping piece 96 in clamping manner by way of the screws 94.

The clamping piece 96, like the securing basis 90, is preferably made of aluminium in order to provide sufficient component strength with at the same time as low a component weight as possible and good thermal conductivity.

The invention claimed is:

1. A pipetting device comprising:
   at least two pipette channels which extend along a channel axis, each of said at least two pipette channels being moveable along the channel axis; and
   a displacement drive coupled to each of said at least two pipette channels and configured to displace each of said at least two pipette channels along a displacement axis which is at a right angle to the channel axis, wherein the displacement along the displacement axis of each of said at least two pipette channels occurs independently of movement along the channel axis and independently of the respectively other said at least two pipette channels displaceable along the displacement axis, the displacement drive including:
   a linear motor including a stator and an armature,
      wherein the stator has at least two magnet arrangements, each of said at least two magnet arrangements including a magnet support supporting a row of magnets which succeed one another along the displacement axis and are arranged with alternating polarity,
      wherein the armature has at least one conductor loop arrangement, the conductor loop arrangement including at least one set of three conductor loops which succeed one another along the displacement axis, of which each conductor loop is configured to be associated with a different phase of a three phase current supply, and
      wherein each pipette channel has at least one conductor loop arrangement, wherein the armatures of directly adjacent pipette channels along the displacement axis are associated with different magnet arrangements and interact therewith.

2. The pipetting device according to claim 1, further comprising a number k, where k is greater than or equal to 2, of magnet arrangements and a number n, where n is greater than or equal to k, of pipette channels, wherein, for each group of k pipette channels which directly succeed one another along the displacement axis, each armature of this group is associated with a different magnet arrangement and interacts therewith.

3. The pipetting device according to claim 1, further comprising four magnet arrangements and at least four pipette channels which may be displaced along the displacement axis and which each have an armature, with each armature of a group of four pipette channels which directly succeed one another along the displacement axis being associated with a different magnet arrangement and interacting therewith.

4. The pipetting device according to claim 1, wherein the pipette channel axes of the pipette channels lie in a common plane extending in the direction of the displacement axis.

5. The pipetting device according to claim 1, further comprising at least two linear guidance rails, wherein the pipette channels whereof the armatures are associated with the same magnet arrangement are guided on the same linear guidance rail, a manner displaceable along the displacement axis.

6. The pipetting device according to claim 5, wherein the number of linear guidance rails is the same as the number of magnet arrangements.

7. The pipetting device according to claim 1, further comprising one or two support profiles extending along the displacement axis, with each support profile supporting two magnet arrangements and two linear guidance rails.

8. The pipetting device according to claim 7, wherein each support profile is constructed substantially symmetrically in relation to a plane of symmetry extending along the displacement axis.

9. The pipetting device according to claim 7, further comprising two parallel support profiles, which are constructed substantially symmetrically in relation to a plane of symmetry extending along the displacement axis and located between the support profiles, wherein the plane of symmetry located between the support profiles preferably contains the channel axes.

10. The pipetting device according to claim 1, characterised in that a magnet arrangement is provided only on one side of a conductor loop arrangement.

11. The pipetting device according to claim 1, wherein the conductor loop arrangement includes specifically one set of three conductor loops that succeed one another along the displacement axis.

12. The pipetting device according to claim 1, wherein the conductor loop arrangement includes a conductor board in which there is provided a recess for all the conductor loops, in which the conductor loops are at least partly accommodated.

13. The pipetting device according to claim 1, wherein the conductor loops of a set succeed one another along the displacement axis without overlap.

14. The pipetting device according to claim 1, wherein the magnets of a magnet arrangement are provided in an orientation such that their direction of polarisation is at a right angle to a plane defined by the channel axis and the displacement axis.

* * * * *